United States Patent
Li et al.

(10) Patent No.: US 9,116,061 B2
(45) Date of Patent: Aug. 25, 2015

(54) DEVICE AND METHOD FOR TESTING PULLING FORCE

(71) Applicants: Fu Tai Hua Industry (Shenzhen) Co., Ltd., Shenzhen (CN); HON HAI PRECISION INDUSTRY CO., LTD., New Taipei (TW)

(72) Inventors: Shi-Bin Li, Shenzhen (CN); Long-Fong Chen, New Taipei (TW); Chung-Yuan Chen, New Taipei (TW); Cai-Jie Li, Shenzhen (CN); Ching-Feng Chen, New Taipei (TW); Guo-Jun Yang, Shenzhen (CN); Ke Chen, Shenzhen (CN); Lin-Hui Cheng, Shenzhen (CN)

(73) Assignees: Fu Tai Hua Industry (Shenzhen) Co., Ltd., Shenzhen (CN); HON HAI PRECISION INDUSTRY CO., LTD., New Taipei (TW)

( * ) Notice: Subject to any disclaimer, the term of this patent is extended or adjusted under 35 U.S.C. 154(b) by 68 days.

(21) Appl. No.: 13/902,892

(22) Filed: May 27, 2013

(65) Prior Publication Data
US 2013/0312534 A1    Nov. 28, 2013

(30) Foreign Application Priority Data
May 28, 2012 (CN) ............... 2012 1 0168422

(51) Int. Cl.
*G01L 1/22* (2006.01)
*G01N 3/08* (2006.01)
*G01L 5/00* (2006.01)

(52) U.S. Cl.
CPC ............... *G01L 1/22* (2013.01); *G01L 5/0033* (2013.01); *G01N 3/08* (2013.01); *G01N 2203/0017* (2013.01); *G01N 2203/0067* (2013.01); *G01N 2203/0296* (2013.01)

(58) Field of Classification Search
CPC  G01L 1/22; G01L 5/0033; G01N 2203/0017; G01N 2203/0296; G01N 3/08; G01N 2203/0067
See application file for complete search history.

(56) References Cited

U.S. PATENT DOCUMENTS

| | | | | |
|---|---|---|---|---|
| 5,111,701 A | * | 5/1992 | Klein | 73/827 |
| 2010/0269564 A1 | * | 10/2010 | Rouse | 73/7 |
| 2010/0307260 A1 | * | 12/2010 | Zhang | 73/838 |

* cited by examiner

*Primary Examiner* — Lisa Caputo
*Assistant Examiner* — Brandi N Hopkins
(74) *Attorney, Agent, or Firm* — Novak Druce Connolly Bove + Quigg LLP (57) ABSTRACT

An exemplary embodiment of a testing device for testing a pulling force includes a shell having a test platform, a load sensor mechanism, a control system, a drive and transmission mechanism and a material clamping mechanism. Two portions of a test object are clasped by the load sensor mechanism and the clamp. When the load sensor mechanism is driven to move further away from the clamp via the drive and transmission mechanism, a pulling force perpendicular to the test platform is generated between the two portions of the test object. The load sensor mechanism detects the pulling force and feeds back the detection to the control system.

19 Claims, 8 Drawing Sheets

DEVICE AND METHOD FOR TESTING PULLING FORCE

BACKGROUND

1. Technical Field

The present disclosure generally relates to a testing device and a method, especially relates to a device and a method for testing a pulling force.

2. Description of Related Art

Flexible flat cables can be integrally welded to a circuit board for making a connection between the flexible flat cable and the circuit board, therefore the reliability of the weld directly affects the connection of the flexible flat cable and the circuit board. A testing process is needed before the assembly of the flexible flat cable and the circuit board is sold. In the testing process, the flexible flat cable and the circuit board are pulled away from each other, and a pulling force is generated. Testers may use a testing device to detect the pulling force and determine the reliability of the weld by whether the welded portion is able to endure a predetermined pulling force, and the integrity of the weld is tested. However, many manual tensile testers use both hands to hold the circuit board and the flat cable to test the integrity of the weld, which is not precise.

What is needed, therefore, is a means which can overcome the described limitations.

BRIEF DESCRIPTION OF THE DRAWINGS

Many aspects of the present embodiments can be better understood with reference to the following drawings. The components in the drawings are not necessarily drawn to scale, the emphasis instead being placed upon clearly illustrating the principles of the present embodiments. Moreover, in the drawings, all the views are schematic, and like reference numerals designate corresponding parts throughout the several views.

DETAILED DESCRIPTION

Reference will be made to the drawings to describe various embodiments.

Figure 1:
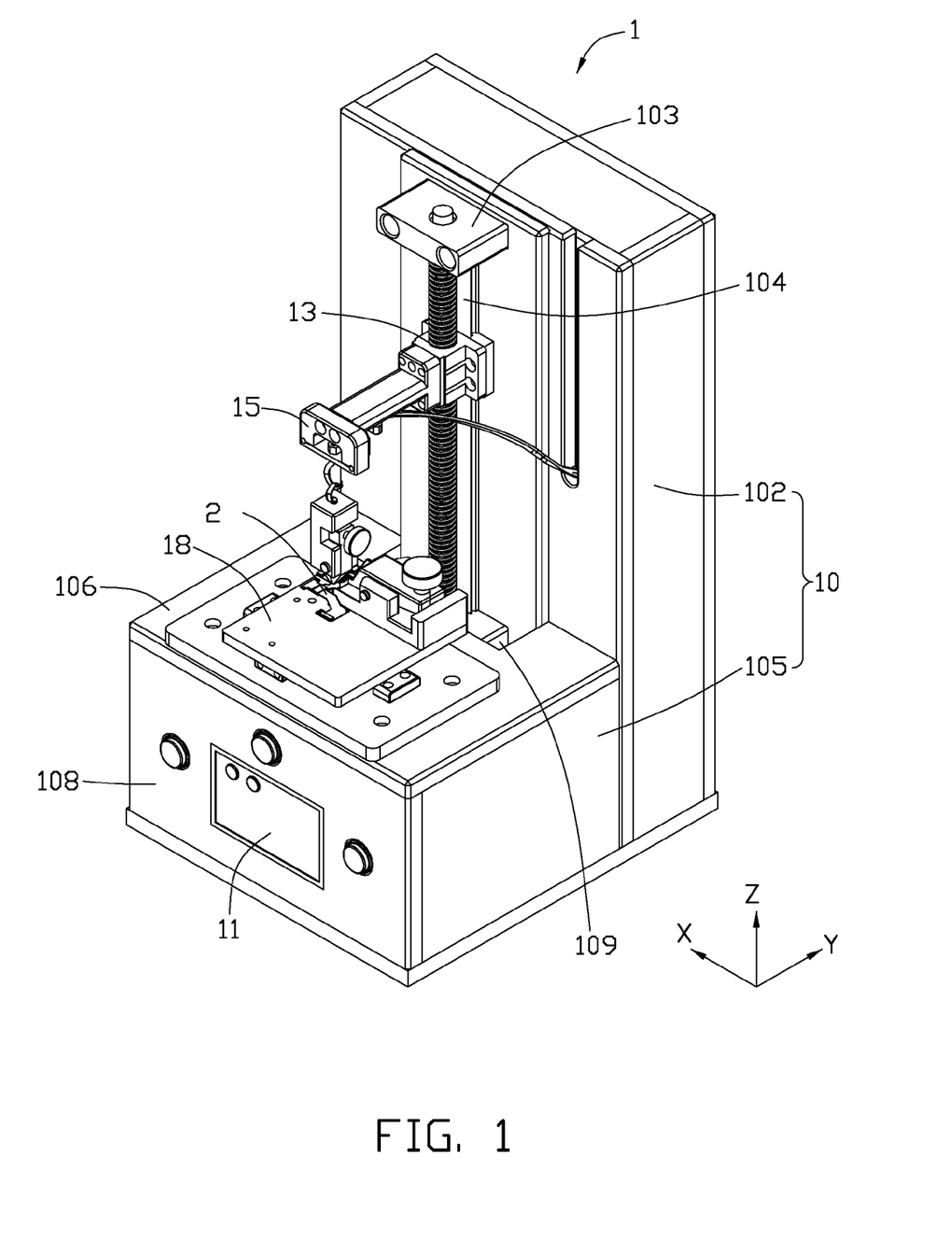
FIG. 1 is an isometric view of a testing device according to an exemplary embodiment of the disclosure, the testing device includes a cabinet, a control console, a control system, a drive and transmission mechanism, a material clamping mechanism, and a load sensor mechanism, and the control system and a part of the drive and transmission mechanism are received in the control console.
Figure 2:
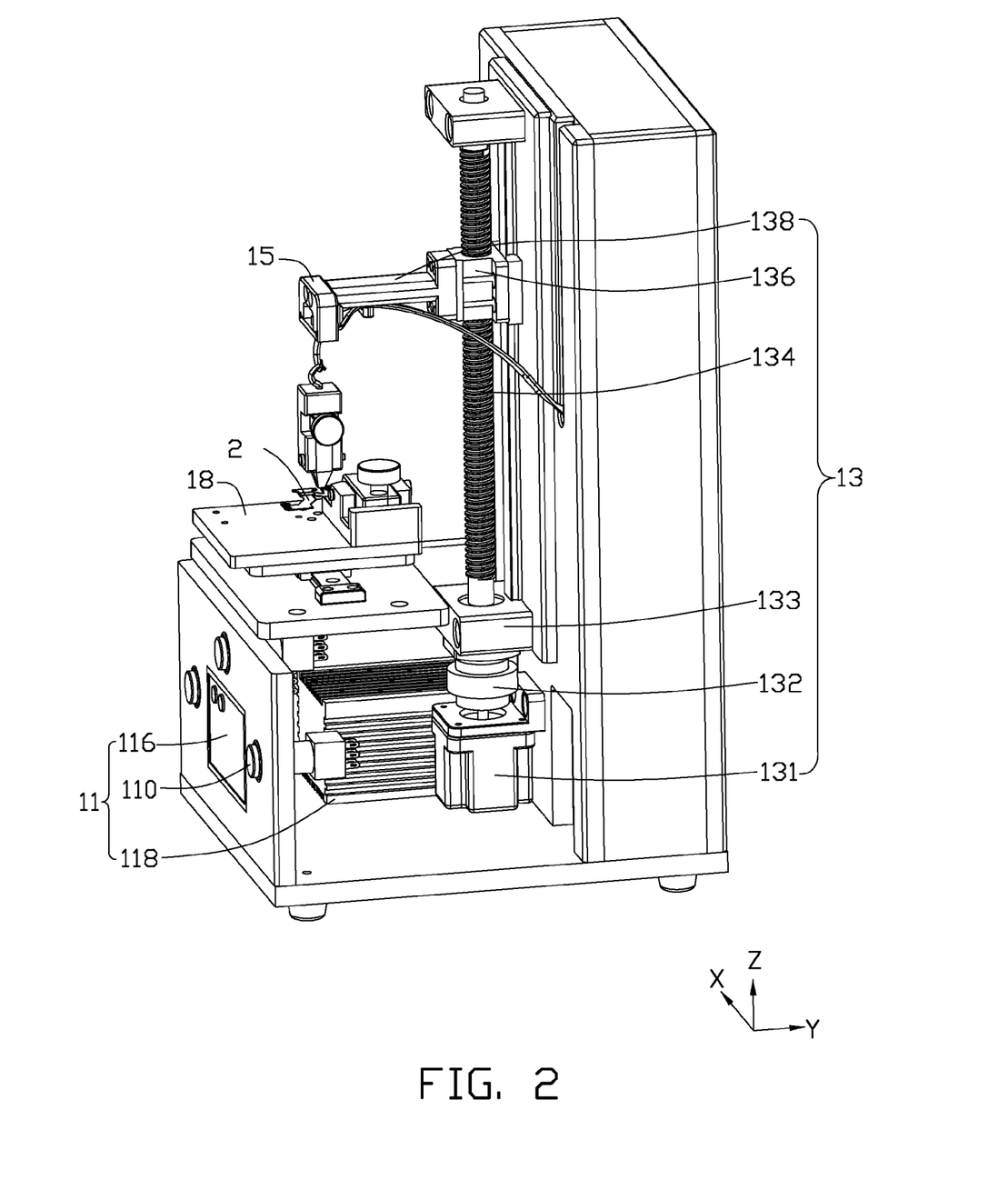
FIG. 2 is an isometric view of the testing device of FIG. 1, and showing the control system and the part of the drive and transmission mechanism exposed from the control console.

FIGS. 1 and 2 are one embodiment of a testing device 1. The testing device 1 is used to test a reliability of a test object 2. The test object 2 includes a first element 21 (see FIG. 5) and a second element 22 (see FIG. 5) integrally welded to the first element 21. For example, the first element 21 may be a circuit board, and the second element 22 may be a flexible flat cable.

The testing device 1 includes a shell 10, a control system 11, a drive and transmission mechanism 13, a load sensor mechanism 15, and a material clamping mechanism 18.

The shell 10 includes a cabinet 102 extending along a first direction and a control console 105 attached to a front side of the cabinet 102, the first direction is a direction parallel to a Z-axis as shown in FIG. 1. The control console 105 and the cabinet 102 form an L profile. The cabinet 102 includes a sliding rail 104 extending along the first direction and a protruding plate 103 extending from a top side of the cabinet 102. The control console 105 includes a test platform 106 perpendicular to the first direction and a connecting plate 108, the test platform 106 interconnecting the cabinet 102 and connecting plate 108. The test platform 106 defines an opening 109 adjacent to the cabinet 102. The protruding plate 103 is parallel to the test platform 106 and corresponds to the opening 109. The sliding rail 104 corresponds to the opening 109 and is positioned below the protruding plate 103.

The control system 11 is received in the control console 105 and includes control buttons 110, a display panel 116 and a programmable logic controller 118. A display screen of the display panel 116 and the control buttons 110 are exposed to the outside of the control console 105 via windows defined at the connecting plate 108 of the control console 105. Therefore, a tester can input operation signals to the control system 11 via the control buttons 110, the tester also can receive a test result of a pulling force detected by the testing device 1 via a display screen of the display panel 116. The programmable logic controller 118 is configured to receive the operation signals and send control signals to the drive and transmission mechanism 13.

The drive and transmission mechanism 13 includes a servo motor 131, a torque controller 132 attached to the servo motor 131, a shaft coupling 133, a screw rod 134 extending along the first direction, a sliding block 136 sleeved on the screw rod 134, and an arm 138 attached to the sliding block 136. The servo motor 131, the torque controller 132, and the shaft coupling 133 are received in the control console 105 and correspond to the opening 109 of the test platform 106. The screw rod 134 comprises a screw thread (not labeled). A first end of the screw rod 134 is inserted into the control console 105 via the opening 109 and is arranged to be coaxial with the torque controller 132 by the shaft coupling 133. A second end of the screw rod 134 is opposite to the first end and rotatably fixed in the protruding plate 103. The drive and transmission mechanism 13 receives the control signals from the control system 11 and drives the servo motor 131 to rotate, the servo motor 131 drives the torque controller 132 and the screw rod 134 to rotate, thus driving the sliding block 136 to move upward or move downward via the screw thread of the screw rod 134. The sliding rail 104 of the cabinet 102 corresponds to the screw rod 134 and is configured to limit the sliding block 136 to move along the sliding rail 104. The arm 138 interconnects the sliding block 136 and the load sensor mechanism 15 and makes the load sensor mechanism 15 position above the test platform 106.

Figure 3:
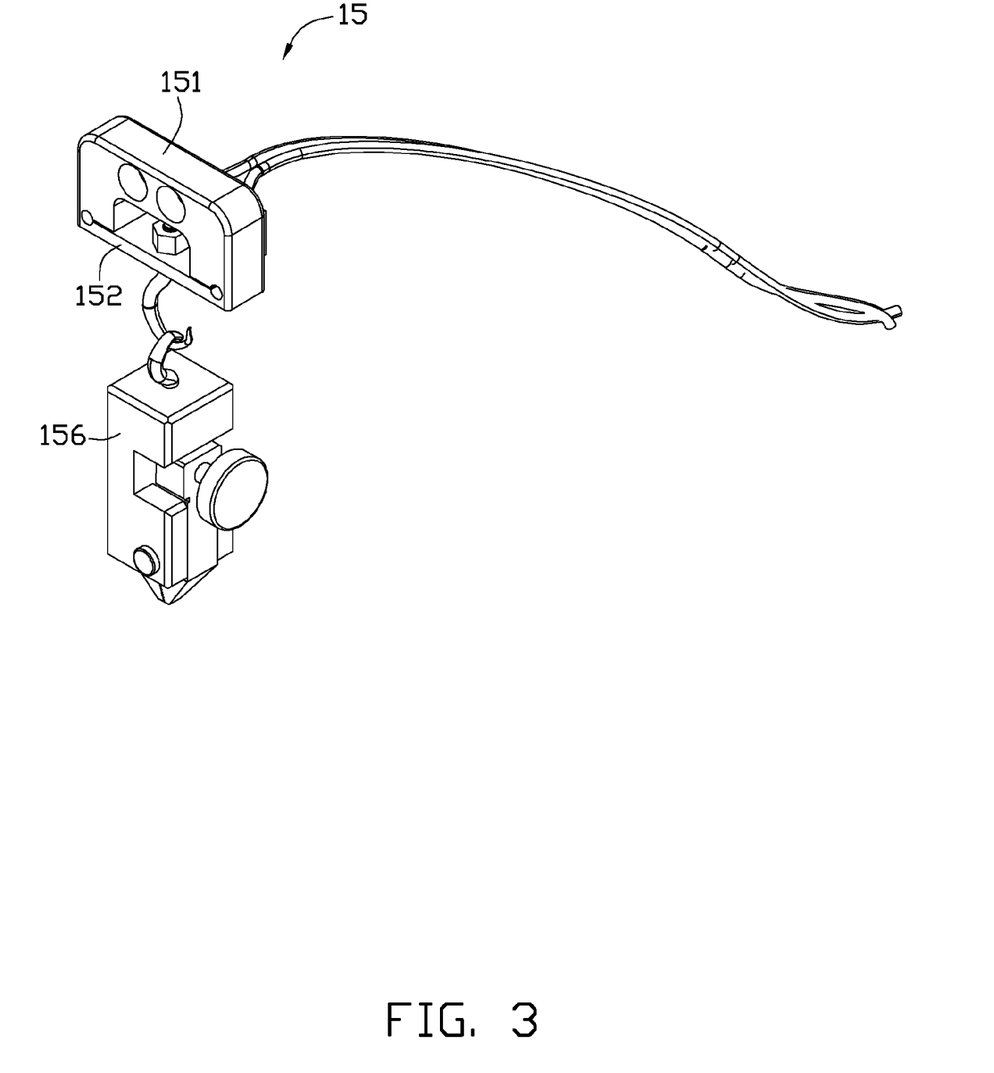
FIG. 3 is an enlarged isometric view of the load sensor mechanism of the testing device of FIG. 1.
Figure 4:
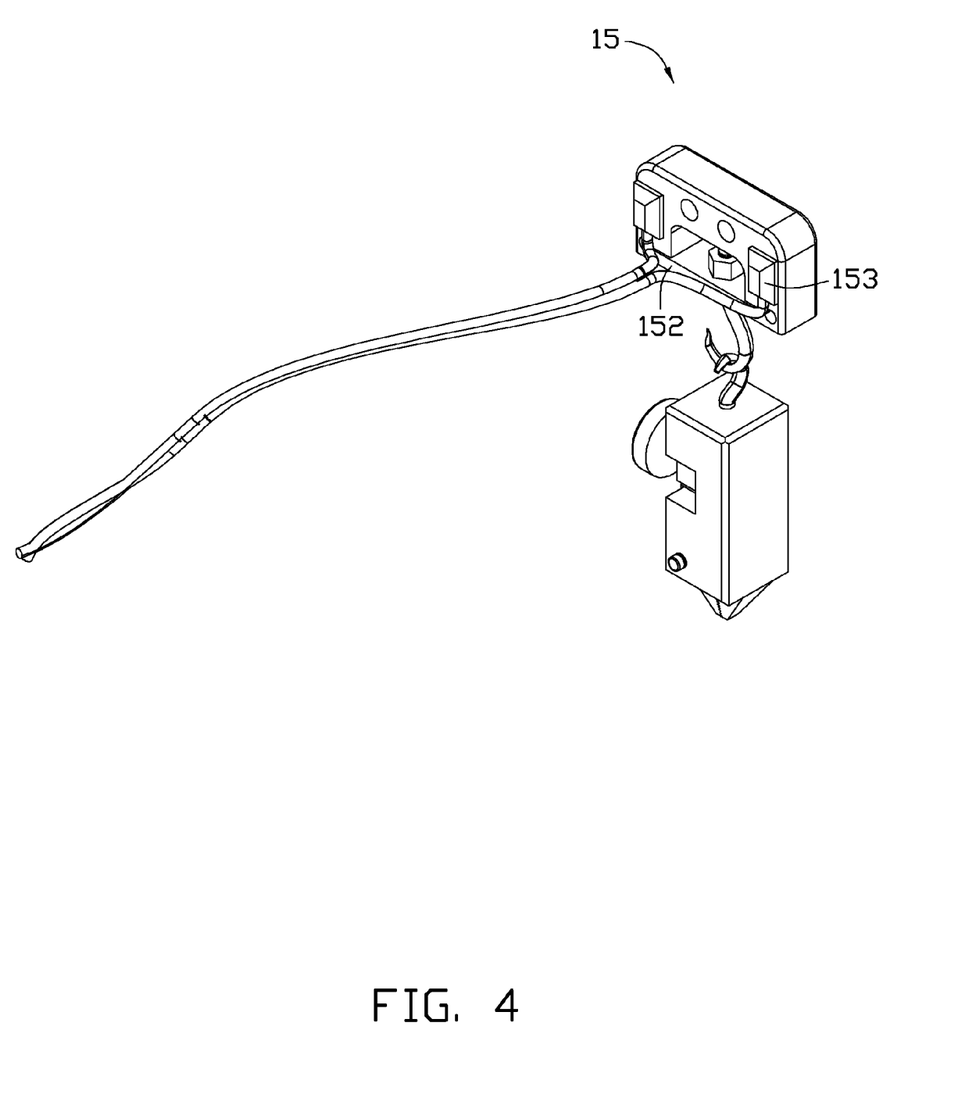
FIG. 4 is similar to FIG. 3, but viewed from another aspect.

FIGS. 3 and 4 show that the load sensor mechanism 15 includes a load sensor device 151 and a clasp mechanism 156 detachably attached to the load sensor device 151. The clasp mechanism 156 is configured to clasp the test object 2. The load sensor device 151 includes a load sensor 153 and an electric resistance strain gauge 152, the clasp mechanism 156 is detachably attached to the electric resistance strain gauge 152, and the electric resistance strain gauge 152 deforms when the electric resistance strain gauge 152 is pulled by the clasp mechanism 156 and shows a change in resistance. The load sensor 153 detects the change in resistance of the electric resistance strain gauge 152, generates a fluctuating current according to the change in resistance, and outputs the fluctuating current to the programmable logic controller 118 of the control system 11. The control system 11 receives the fluctuating current, calculates the value of the pulling force according the fluctuating current, and displays the value of the pulling force via the display panel 116.

Figure 5:
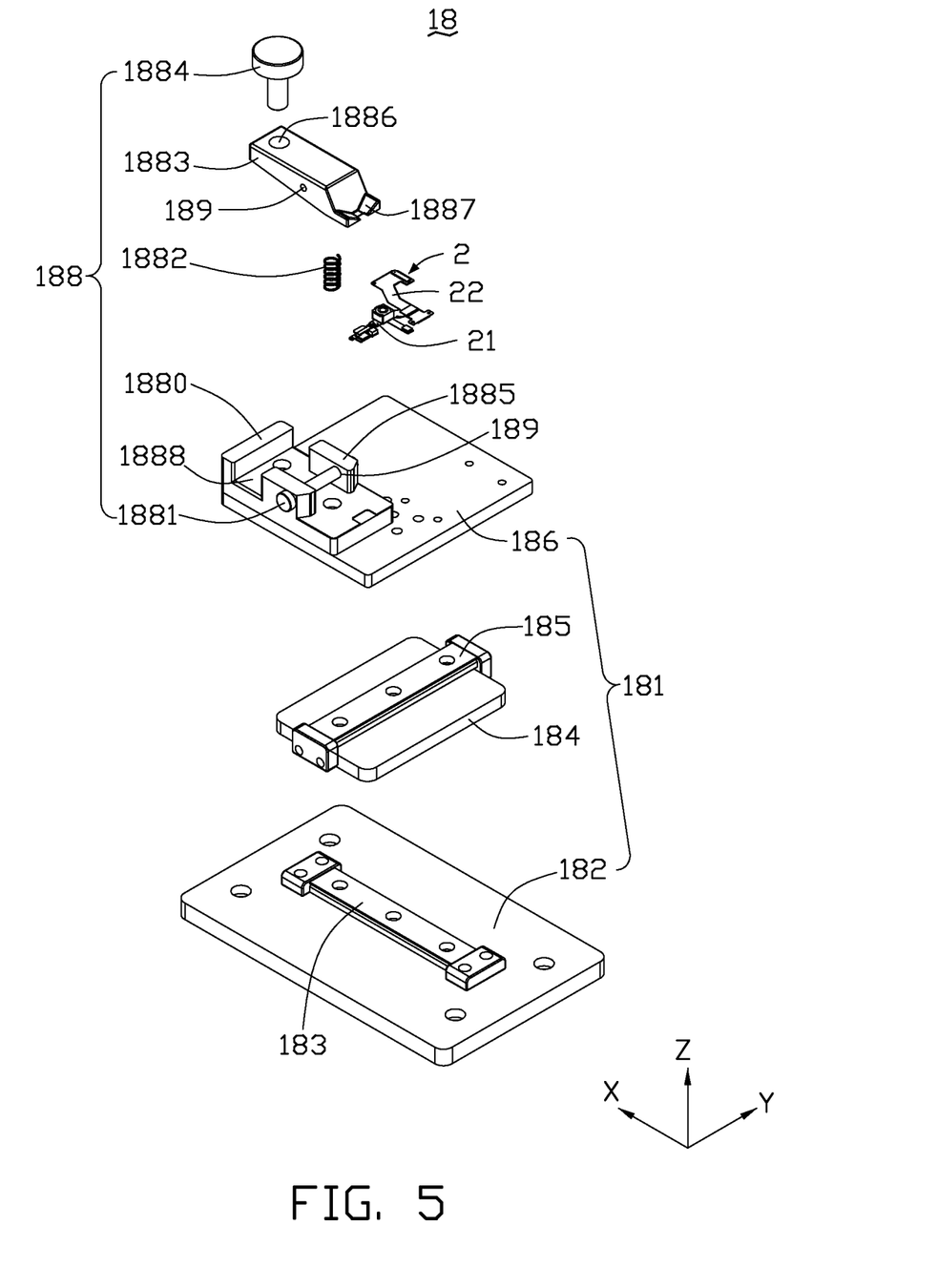
FIG. 5 is an exploded, isometric view of the material clamping mechanism of the testing device of FIG. 1.

FIG. 5 shows that the material clamping mechanism 18 includes a positioning device 181 attached to the test platform 106 and a clamp 188 attached to the positioning device 181. The positioning device 181 is configured to adjust the location of the clamp 188, thus making the clamp 188 align with the load sensor mechanism 15. The clamp 188 is configured to clasp the test object 2.

The positioning device 181 includes a first position plate 182, a second position plate 184 and a clamp platform 186. The first position plate 182 is fixed to the test platform 106 and includes a first rail 183 extending along a second direction perpendicular to the first direction, and the second direction is a direction parallel to an X-axis as shown in FIG. 5. The second position plate 184 slidably attaches to the first position plate 182 and is configured to move back and forth along the first rail 183. The second position plate 184 includes a second rail 185 extending along a third direction perpendicular to the first and second direction, and the third direction is a direction parallel to a Y-axis as shown in FIG. 5. The clamp platform 186 slidably attaches to the second position plate 184 and is configured to move back and forth along the second rail 185. The clamp 188 is fixed to the clamp platform 186.

The clamp 188 includes a main body 1880, a pressing body 1883, a fixing rod 1881, an elastic member 1882, and a fixing bolt 1884. The main body 1880 includes a fixing plate 1888 fixed to the clamp platform 186 and two vertical plates 1885 perpendicularly extending from the fixing plate 1888. Each vertical plate 1885 defines a through hole 189. The fixing rod 1881 extends perpendicularly to the vertical plates 1885.

The pressing body 1883 is located between the two vertical plates 1885 and defines a through hole 189 extending perpendicular to the vertical plate 1885. The fixing rod 1881 passes through the through holes 189 of the vertical plates 1885 and the pressing body 1883 and rotatably fixes the pressing body 1883 to the main body 1880. The pressing body 1883 serves as a seesaw. The pressing body 1883 includes a first side and a second side opposite to the first side. A pressing nozzle 1887 is attached to the pressing body 1883 at the second side, and the pressing nozzle 1887 defines a notch. The fixing bolt 1884 passes through the pressing body 1883 at the first side by screwing and is further screwed in the fixing plate 1888. The elastic member 1882 is arranged between the pressing body 1883 and the fixing plate 1888 on the second side, and applies a resilient force to the pressing body 1883 when the pressing body 1883 is moved. When the fixing bolt 1884 rotates, the fixing bolt 1884 drives the first side of the pressing body 1883 to move upward or move downward along the first direction, thus driving the pressing nozzle 1887 to move closer to the fixing plate 1888 or move further away from the fixing plate 1888. When the pressing nozzle 1887 moves closer to the fixing plate 1888, the clamp 188 is at a clasped state (see FIG. 7), the first element of the test object 2 can be clasped by the pressing nozzle 1887, and the second element of the test object can extend out of the pressing nozzle 1887 via the notch of the pressing nozzle 1887. When the pressing nozzle 1887 moves away from the fixing plate 1888, the clamp 188 is at an open state, and the test object 2 can be taken out from the clamp 188 (see FIG. 6).

Figure 6:
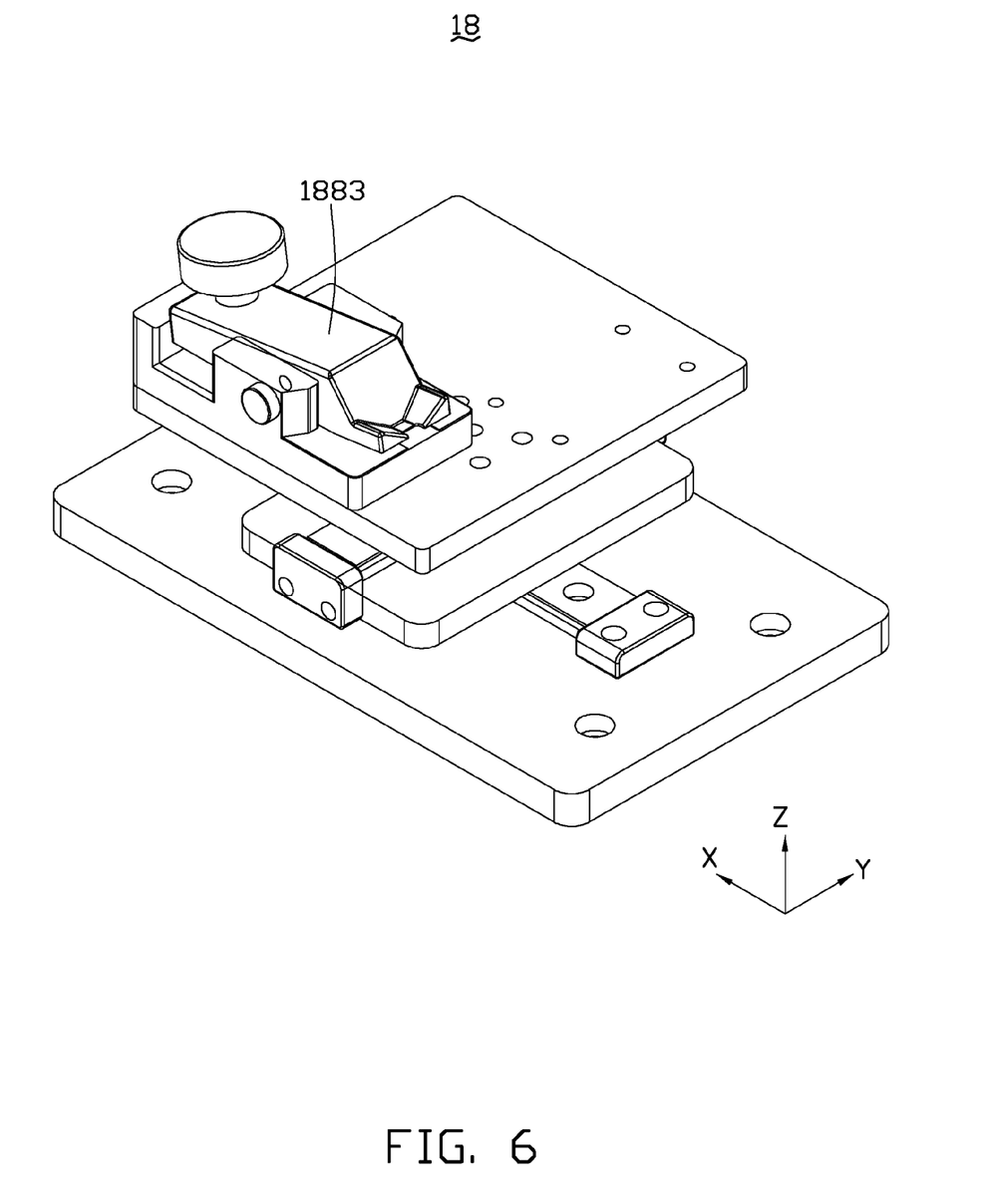
FIG. 6 is an assembled view of the material clamping mechanism of FIG. 5, wherein the material clamping mechanism includes a positioning device and a clamp, and showing the clamp in an open state.
Figure 7:
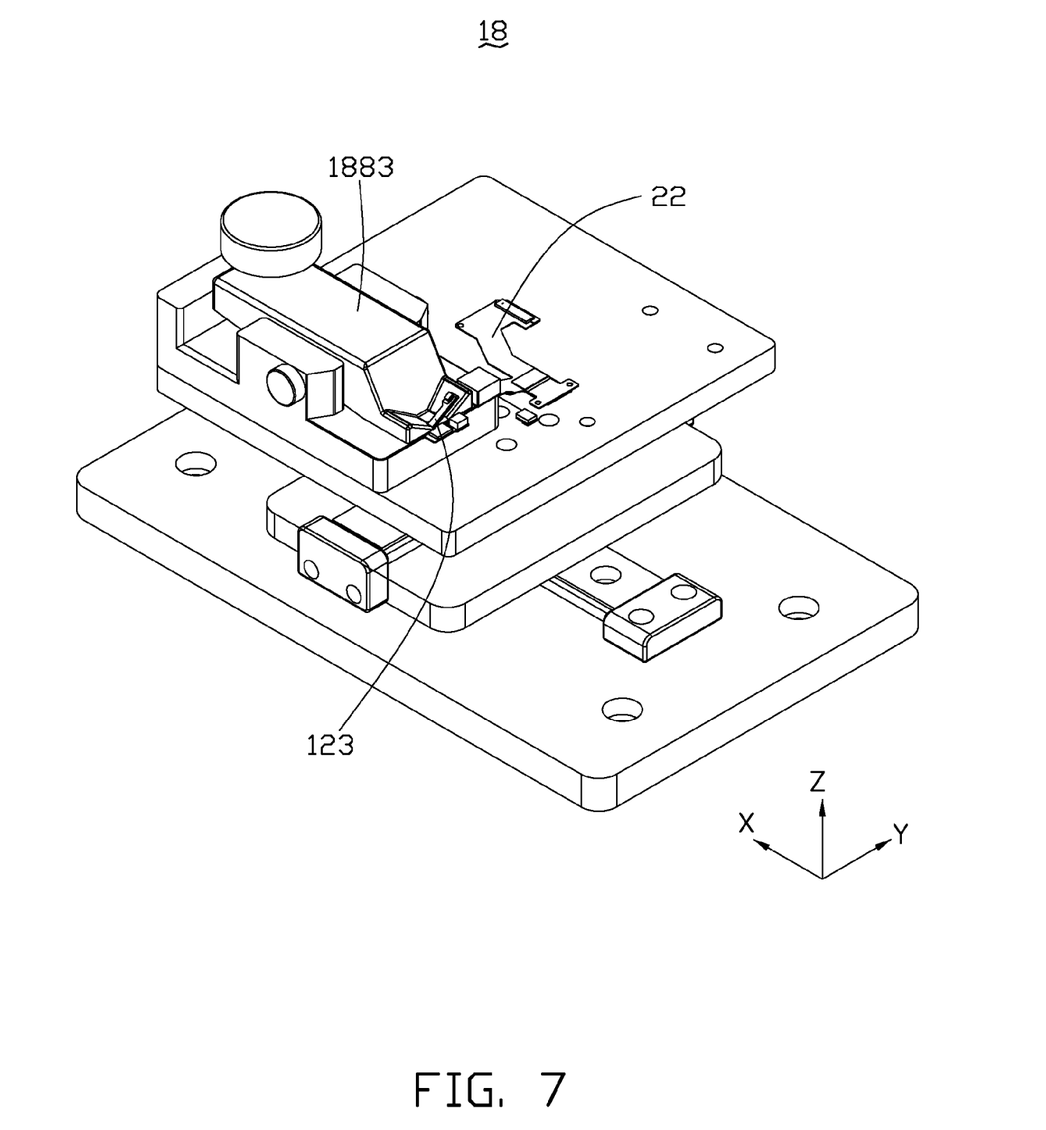
FIG. 7 is similar to FIG. 6, but showing the clamp in a clasped state.

When the testing device 1 is used, the tester rotates the fixing bolt 1884, opening the clamp 188. The first element of the test object 2 is inserted between the pressing body 1883 and the fixing plate 1888. The welded portion of the test object 2 corresponds to the notch of the pressing nozzle 1887, and the second element of the test object 2 extends out of the pressing nozzle 1887 via the notch and positions above the pressing nozzle 1887. Then the fixing bolt 1884 is rotated to clasp the clamp 188, the first element of the test object 2 is firmly pressed below the pressing nozzle 1887, therefore the pressing nozzle 1887 clasps the first element of the test object 2. The location of the clamp 188 is adjusted by sliding the second position plate 184 and the clamp platform 186, thus making the welded portion of the test object 2 align with the clasp mechanism 156 of the load sensor mechanism 15. The second element of the test object 2 is clasped by the clasp mechanism 156.

When the first and second elements of the test object 2 are clasped by the clamp 188 and the clasp mechanism 156, the tester inputs operation signals via control buttons 110 to rotate the servo motor 131, rotating the torque controller 132 and the screw rod 134, and thus moving the sliding block 136 upward and downward along the first direction. The load sensor mechanism 15 moves further away in unison with the sliding block 136 from the clamp 188 or moves closer to the clamp 188. When the load sensor mechanism 15 moves further away from the clamp 188, the pulling force along the first direction is generated at the welded portion of the test object 2. The testing device 1 detects the pulling force and outputs the value of the pulling force via the display panel 116. The pulling force is gradually increased when the load sensor mechanism 15 moves further away from the clamp 188. When the pulling force of the test object 2 equal to a predetermined pulling force, the tester inputs operation signals to stop the rotation of the servo motor 131, and determine the reliability of the weld by whether the welded portion of the test object 2 is able to endure the predetermined pulling force.

The testing device 1 has a measurement range, when the pulling force is greater than the maximum of the measurement range, the torque controller 132 rotates and stops to drive the screw rod 134 to rotate.

Figure 8:
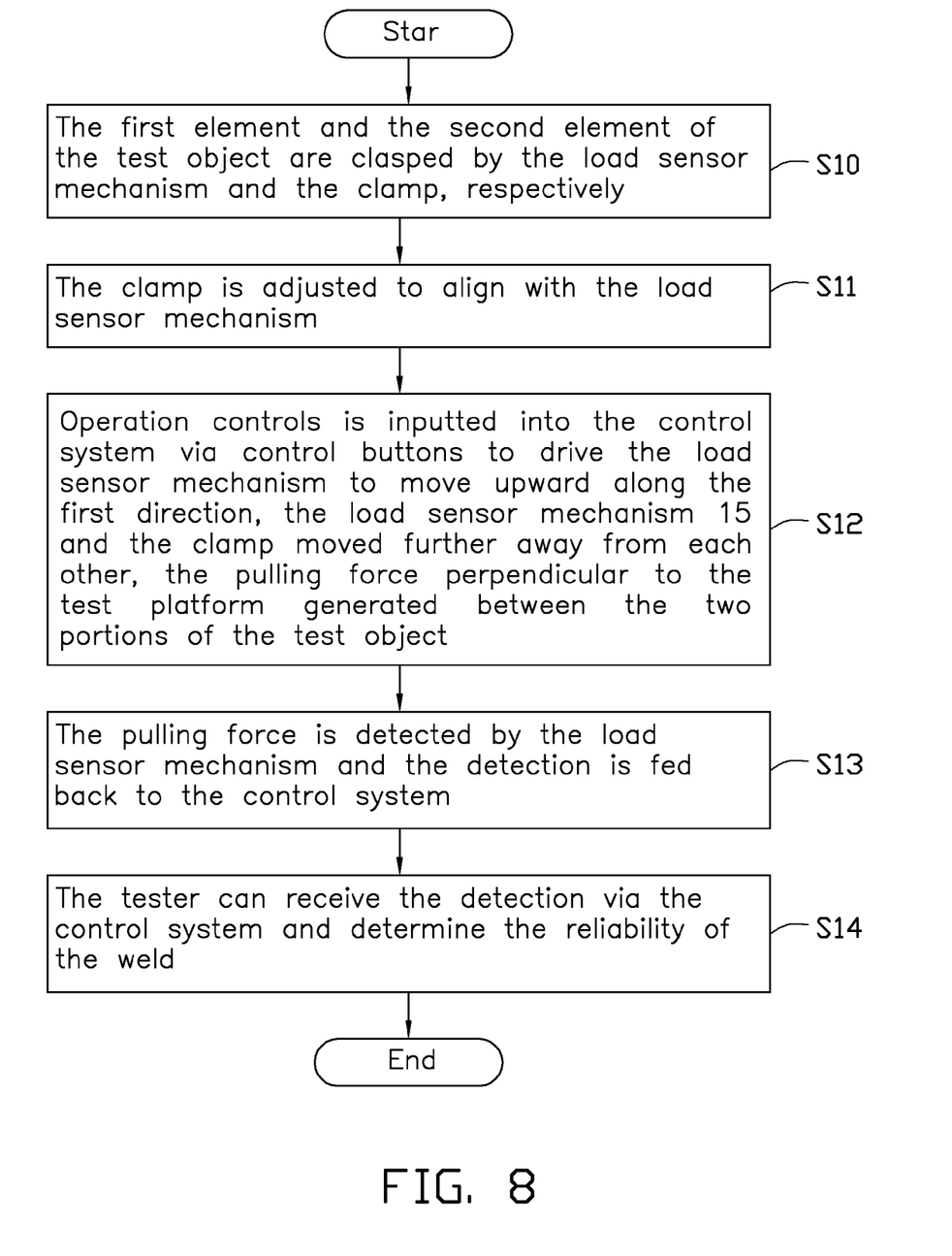
FIG. 8 is a flowchart of steps S10-S14 of a testing method utilizing the testing device in FIG. 1.

FIG. 8 shows a flowchart summarizing a method for testing the pulling force of the test object 2 according to an exemplary embodiment of the present disclosure. The testing steps are described below.

In step S10, the first element and the second element of the test object are clasped by the load sensor mechanism and the clamp, respectively.

In step S11, the clamp 188 is adjusted to align with the load sensor mechanism 15.

In step S12, operation controls is inputted into the control system 11 via control buttons 110 to drive the load sensor mechanism 15 to move upward along the first direction, the load sensor mechanism 15 and the clamp 188 moved further away from each other, the pulling force perpendicular to the test platform 106 generated between the two portions of the test object.

In step S13, the pulling force is detected by the load sensor mechanism 15 and the detection is fed back to the control system 11.

In step S14, the tester can receive the detection via the control system and determine the reliability of the weld.

With the above-described configuration, the tester can use the testing device 1 to detect the pulling force of the test object, the user only needs to input operation signals via the control buttons 110, and the testing result is consistently precise.

The testing device 1 is not limited to the above-described configuration, the positioning device only has only one position plate, the first rail is arranged on the test platform, and the second rail is arranged on only one position plate.

It is believed that the present embodiments and their advantages will be understood from the foregoing description, and it will be apparent that various changes may be made thereto without departing from the spirit and scope of the description or sacrificing all of their material advantages, the examples hereinbefore described merely being exemplary embodiments.

What is claimed is:

1. A testing device for testing a pulling force, comprising:
   a shell comprising a test platform;
   a load sensor mechanism;
   a control system configured to receive operation signals from a tester and send a control signal;
   a drive and transmission mechanism configured to receive the control signal and drive the load sensor mechanism to move upward or move downward along a first direction perpendicular to the test platform; and
   a material clamping mechanism comprising a positioning device arranged on the test platform and a clamp, the positioning device configured to adjust the location of the clamp to align with the load sensor mechanism;
   wherein two portions of a test object are clasped by the load sensor mechanism and the clamp, respectively, when the load sensor mechanism is driven to move upward along the first direction, the load sensor mechanism and the clamp move further away from each other, a pulling force perpendicular to the test platform is generated between the two portions of the test object, the load sensor mechanism detects the pulling force and feeds back the detection to the control system.

2. The testing device of claim 1, wherein the load sensor mechanism comprises a load sensor device and a clasp mechanism for clasping the test object,
   the load sensor device comprises a load sensor and an electric resistance strain gauge, the clasp mechanism is detachably attached to the electric resistance strain gauge,
   the electric resistance strain gauge deforms when the electric resistance strain gauge is pulled by the test object and the clasp mechanism and shows a change in resistance,
   the load sensor detects the change and generates a fluctuating current, and outputs the fluctuating current to the control system, the control system receives the fluctuating current, calculates a value of the pulling force according to the fluctuating current, and displays the value of the pulling force.

3. The testing device of claim 2, wherein the control system comprises control buttons, a display panel, and a programmable logic controller,
   the tester inputs operation signals via the control buttons, the programmable logic controller receives the operation signals and sends the control signals to the drive and transmission mechanism, and the display panel is configured to display the value of the pulling force.

4. The testing device of claim 3, wherein the drive and transmission mechanism comprises a servo motor, a screw rod, and a sliding block sleeved on the screw rod by screwing,
   the screw rod extends along the first direction,
   the control system drives the servo motor to rotate,
   the servo motor drives the screw rod to rotate, the screw rod drives the sliding block to move upward or move downward along the first direction perpendicular to the test platform, and the load sensor mechanism moves upward or moves downward in unison with the sliding block.

5. The testing device of claim 4, wherein the drive and transmission mechanism further comprises an arm perpendicular to the screw rod, the arm interconnects the sliding block and the load sensor mechanism, and positions the load sensor mechanism above the test platform.

6. The testing device of claim 4, wherein the drive and transmission mechanism further comprises a torque controller attached to the servo motor,
   the servo motor drives the screw rod to rotate via the torque controller,
   the testing device comprises a measurement range, when the pulling force is greater than a maximum of the measurement range of the testing device, the torque controller rotates and stops to drive the screw rod to rotate.

7. The testing device of claim 6, wherein the shell comprises a cabinet extending along the first direction and a control console attached to a front side of the cabinet,
   the control console and the cabinet form an L profile, the cabinet comprises a sliding rail extending along the first direction and a protruding plate extending from a top side of the cabinet,
   the control console comprises the test platform and a connecting plate, and the test platform interconnects the cabinet and connecting plate, the test platform defines an opening adjacent to the cabinet,
   the protruding plate is parallel to the test platform and corresponds to the opening, the sliding rail corresponds to the opening and locates below the protruding plate,
   the control system, the servo motor, and the torque controller are received in the control console and correspond to the opening of the test platform,
   a first end of the screw rod is inserted into the control console via the opening and is arranged to be coaxial with the torque controller by a shaft coupling,
   a second end of the screw rod is opposite to the first end and is rotatably fixed in the protruding plate.

8. A testing device for testing a pulling force, comprising:
   a shell comprising a test platform;
   a load sensor mechanism;
   a control system configured to receive operation signals from a tester and send a control signal;
   a drive and transmission mechanism configured to receive the control signal and drive the load sensor mechanism to move upward or move downward along a first direction perpendicular to the test platform; and
   a material clamping mechanism comprising a positioning device arranged on the test platform and a clamp, the positioning device configured to adjust the location of the clamp to align with the load sensor mechanism;
   wherein two portions of a test object are clasped by the load sensor mechanism and the clamp, respectively, when the load sensor mechanism is driven to move upward along the first direction, the load sensor mechanism and the clamp move further away from each other, a pulling force perpendicular to the test platform is generated between the two portions of the test object, the load sensor mechanism detects the pulling force and feeds back the detection to the control system;
   the test object comprises a first element and a second element, the second element is integrally welded to the first element, the first element is clasped by the clamp of the material clamping mechanism, and the second element is clasped by the load sensor mechanism.

9. The testing device of claim 8, wherein the positioning device comprises a first position plate, a second position plate and a clamp platform,
the first position plate is fixed to the test platform and comprises a first rail extending along a second direction perpendicular to the first direction,
the second position plate is slidably attached to the first position plate and configured to move back and forth along the second direction,
the second position plate comprises a second rail extending along a third direction perpendicular to the first and second direction,
the clamp platform is slidably attached to the second position plate and configured to move back and forth along the third direction, and the clamp is fixed to the clamp platform.

10. The testing device of claim 9, wherein the clamp comprises a main body, a pressing body, a fixing rod, an elastic member, and a fixing bolt,
the main body comprises a fixing plate fixed to the clamp platform, two vertical plates perpendicularly extend from the fixing plate, each of the vertical plate defines a through hole, the pressing body defines a through hole,
the fixing rod is perpendicular to the vertical plates,
the fixing rod passes through the through holes of the vertical plates and the pressing body and rotatably fixes the pressing body between the two vertical plates,
the pressing body comprises a first side and a second side opposite to the first side, a pressing nozzle is attached to the pressing body at the second side, and the pressing nozzle defines a notch,
the fixing bolt passes through the pressing body at the first side of the pressing body by screwing and is screwed in the fixing plate,
the elastic member is arranged between the pressing body and the fixing plate on the second side, and applies a resilient force to the pressing body when the pressing body is moved,
when the fixing bolt rotates, the fixing bolt drives the first side of the pressing body to move upward or move downward along the first direction, thus driving the pressing nozzle to move closer to the fixing plate or move further away from the fixing plate,
when the pressing nozzle moves closer to the fixing plate, the clamp in a clasped state, a portion of the test object can be clasped by the pressing nozzle, and the other portion of the test object can extend out of the pressing nozzle via the notch and be clasped by the clasp mechanism of the load sensor mechanism,
when the pressing nozzle moves away from the fixing plate, the clamp is at an open state, and the test object can be taken out from the clamp.

11. A testing method for testing a pulling force of a test object, comprising:
providing a testing device, the testing device configured to detect a pulling force generated between two portions of a test object, the testing device comprising a shell, a load sensor mechanism, a control system, a drive and transmission mechanism, a material clamping mechanism, the shell comprising a test platform, the control system configured to receive operation signals from a tester and send a control signal, the drive and transmission mechanism configured to receive the control signal and drive the load sensor mechanism to move upward or move downward along a first direction perpendicular to the test platform, the material clamping mechanism comprising a positioning device arranged on the test platform and a clamp, the positioning device configured to adjust the location of the clamp to align with the load sensor mechanism;
making the load sensor mechanism and the clamp to clasp the two portions of the test object, respectively;
making the clamp to align with the load sensor mechanism;
inputting operation controls via the control system to drive the load sensor mechanism to move upward along the first direction, the load sensor mechanism and the clamp moved further away from each other, a pulling force perpendicular to the test platform generated between the two portions of the test object;
detecting the pulling force and feeding back the detection to the control system via the load sensor mechanism; and
receiving the detection via the control system,
wherein the test object comprises a first element and a second element, the second element is integrally welded to the first element, the first element is clasped by the clamp of the material clamping mechanism, and the second element is clasped by the load sensor mechanism.

12. The testing method of claim 11, wherein the load sensor mechanism comprises a load sensor device and a clasp mechanism for clasping the test object,
the load sensor device comprises a load sensor and an electric resistance strain gauge, the clasp mechanism is detachably attached to the electric resistance strain gauge,
the electric resistance strain gauge deforms when the electric resistance strain gauge is pulled by the test object and the clasp mechanism and shows a change in resistance,
the load sensor detects the change and generates a fluctuating current, and outputs the fluctuating current to the control system, the control system receives the fluctuating current, calculates a value of the pulling force according to the fluctuating current, and displays the value of the pulling force.

13. The testing method of claim 12, wherein the control system comprises control buttons, a display panel, and a programmable logic controller,
the tester inputs operation signals via the control buttons, the programmable logic controller receives the operation signals and sends the control signals to the drive and transmission mechanism, and the display panel is configured to display the value of the pulling force.

14. The testing method of claim 13, wherein the drive and transmission mechanism comprises a servo motor, a screw rod, and a sliding block sleeved on the screw rod by screwing,
the screw rod extends along the first direction, the control system drives the servo motor to rotate, the servo motor drives the screw rod to rotate, the screw rod drives the sliding block to move upward or move downward along the first direction perpendicular to the test platform, and the load sensor mechanism moves upward or moves downward in unison with the sliding block.

15. The testing method of claim 14, wherein the drive and transmission mechanism further comprises an arm perpendicular to the screw rod, the arm interconnects the sliding block and the load sensor mechanism, and positions the load sensor mechanism above the test platform.

16. The testing method of claim 14, wherein the drive and transmission mechanism further comprises a torque controller attached to the servo motor, the servo motor drives the screw rod to rotate via the torque controller, the testing device comprises a measurement range, when the pulling force is greater than a maximum of the measurement range of the testing device, the torque controller rotates and stops to drive the screw rod to rotate.

17. The testing method of claim 16, wherein the shell comprises a cabinet extending along the first direction and a control console attached to a front side of the cabinet, the control console and the cabinet form an L profile, the cabinet comprises a sliding rail extending along the first direction and a protruding plate extending from a top side of the cabinet, the control console comprises the test platform and a connecting plate, and the test platform interconnects the cabinet and connecting plate, the test platform defines an opening adjacent to the cabinet, the protruding plate is parallel to the test platform and corresponds to the opening, the sliding rail corresponds to the opening and locates below the protruding plate, the control system, the servo motor, and the torque controller are received in the control console and correspond to the opening of the test platform, a first end of the screw rod is inserted into the control console via the opening and is arranged to be coaxial with the torque controller by a shaft coupling, a second end of the screw rod is opposite to the first end and is rotatably fixed in the protruding plate.

18. The testing method of claim 11, wherein the positioning device comprises a first position plate, a second position plate and a clamp platform, the first position plate is fixed to the test platform and comprises a first rail extending along a second direction perpendicular to the first direction, the second position plate is slidably attached to the first position plate and configured to move back and forth along the second direction, the second position plate comprises a second rail extending along a third direction perpendicular to the first and second direction, the clamp platform is slidably attached to the second position plate and configured to move back and forth along the third direction, and the clamp is fixed to the clamp platform.

19. The testing method of claim 11, wherein the clamp comprises a main body, a pressing body, a fixing rod, an elastic member, and a fixing bolt, the main body comprises a fixing plate fixed to the clamp platform, two vertical plates perpendicularly extend from the fixing plate, each of the vertical plate defines a through hole, the pressing body defines a through hole, the fixing rod is perpendicular to the vertical plates, the fixing rod passes through the through holes of the vertical plates and the pressing body and rotatably fixes the pressing body between the two vertical plates, the pressing body comprises a first side and a second side opposite to the first side, a pressing nozzle is attached to the pressing body at the second side, and the pressing nozzle defines a notch, the fixing bolt passes through the pressing body at the first side of the pressing body by screwing and is screwed in the fixing plate, the elastic member is arranged between the pressing body and the fixing plate on the second side, and applies a resilient force to the pressing body when the pressing body is moved, when the fixing bolt rotates, the fixing bolt drives the first side of the pressing body to move upward or move downward along the first direction, thus driving the pressing nozzle to move closer to the fixing plate or move further away from the fixing plate, when the pressing nozzle moves closer to the fixing plate, the clamp in a clasped state, a portion of the test object can be clasped by the pressing nozzle, and the other portion of the test object can extend out of the pressing nozzle via the notch and be clasped by the clasp mechanism of the load sensor mechanism, when the pressing nozzle moves away from the fixing plate, the clamp in an open state, and the test object can be taken out from the clamp.

* * * * *